(12) United States Patent
Kawabata et al.

(10) Patent No.: US 12,136,475 B2
(45) Date of Patent: Nov. 5, 2024

(54) MEDICAL INFORMATION MANAGEMENT APPARATUS, MEDICAL INFORMATION MANAGEMENT METHOD, AND MEDICAL INFORMATION MANAGEMENT PROGRAM

(71) Applicant: Konica Minolta, Inc., Tokyo (JP)

(72) Inventors: Akihiro Kawabata, Hachioji (JP); Jo Shikama, Machida (JP)

(73) Assignee: Konica Minolta, Inc., Tokyo (JP)

( * ) Notice: Subject to any disclaimer, the term of this patent is extended or adjusted under 35 U.S.C. 154(b) by 241 days.

(21) Appl. No.: 17/652,587

(22) Filed: Feb. 25, 2022

(65) Prior Publication Data

US 2022/0284997 A1    Sep. 8, 2022

(30) Foreign Application Priority Data

Mar. 5, 2021   (JP) .................. 2021-035172

(51) Int. Cl.
*G16H 10/60*   (2018.01)

(52) U.S. Cl.
CPC .................. *G16H 10/60* (2018.01)

(58) Field of Classification Search
CPC .................................................. G16H 10/60
See application file for complete search history.

(56) References Cited

U.S. PATENT DOCUMENTS

| | | | | |
|---|---|---|---|---|
| 6,252,599 B1* | 6/2001 | Natsuko | ............... | G06T 19/006 345/419 |
| 6,524,246 B1* | 2/2003 | Kelly | ............... | A61B 8/085 600/437 |
| 6,937,776 B2* | 8/2005 | Li | ............... | G06T 7/0012 382/131 |
| 7,123,762 B2* | 10/2006 | Giger | ............... | G06V 10/25 600/408 |
| 7,398,256 B2* | 7/2008 | Farhat | ............... | G06N 3/02 706/12 |
| 7,418,123 B2* | 8/2008 | Giger | ............... | G06T 7/0012 382/132 |
| 7,697,742 B2* | 4/2010 | Dehmeshki | ............... | G06V 10/267 600/443 |

(Continued)

FOREIGN PATENT DOCUMENTS

| | | |
|---|---|---|
| JP | 2008-237426 A | 10/2008 |
| JP | 2012-217631 A | 11/2012 |

(Continued)

OTHER PUBLICATIONS

Schneider, Jan. 2022, Chapter 13.*

(Continued)

*Primary Examiner* — Michael I Ezewoko
(74) *Attorney, Agent, or Firm* — LUCAS & MERCANTI, LLP

(57) ABSTRACT

A medical information management apparatus includes a hardware processor that: generates first medical information that does not include subject identification information that uniquely identifies a subject on a basis of medical image information regarding the subject; generates second medical information that includes the subject identification information on a basis of the medical image information; and causes the first medical information that has been generated to be stored in a first medical information storage part.

12 Claims, 4 Drawing Sheets

(56) References Cited

U.S. PATENT DOCUMENTS

| | | | | |
|---|---|---|---|---|
| 7,813,822 | B1* | 10/2010 | Hoffberg | H04N 7/163 |
| | | | | 381/73.1 |
| 8,121,362 | B2* | 2/2012 | Zhan | G06V 10/24 |
| | | | | 382/128 |
| 8,303,505 | B2* | 11/2012 | Webler | G06T 7/38 |
| | | | | 600/447 |
| 8,718,747 | B2* | 5/2014 | Bjornerud | A61B 6/481 |
| | | | | 600/431 |
| 8,798,714 | B2* | 8/2014 | Henning | A61B 5/0205 |
| | | | | 600/407 |
| 8,878,393 | B2* | 11/2014 | Kirby | H02J 50/70 |
| | | | | 307/104 |
| 9,165,360 | B1* | 10/2015 | Bates | G06T 7/11 |
| 9,184,632 | B2* | 11/2015 | Kirby | H01Q 1/2225 |
| 9,307,949 | B2* | 4/2016 | Tsubota | G06T 11/005 |
| 9,569,736 | B1* | 2/2017 | Ghesu | G06N 20/00 |
| 9,579,518 | B2* | 2/2017 | Gertner | A61B 6/032 |
| 9,760,978 | B1* | 9/2017 | Lu | G06T 5/50 |
| 9,808,174 | B2* | 11/2017 | Kokubun | G01R 33/4824 |
| 9,986,968 | B2* | 6/2018 | Slak | A61B 8/5261 |
| 10,016,622 | B2* | 7/2018 | Kim | A61N 5/1031 |
| 10,032,250 | B2* | 7/2018 | Mazurkewitz | G01R 33/56509 |
| 10,463,322 | B2* | 11/2019 | Pang | A61B 6/547 |
| 10,677,871 | B2* | 6/2020 | Helle | G01R 33/5635 |
| 10,684,341 | B2* | 6/2020 | Helle | G01R 33/56316 |
| 10,729,408 | B2* | 8/2020 | Matsunaga | A61B 8/488 |
| 10,748,280 | B2* | 8/2020 | Meng | G06T 7/0012 |
| 10,830,858 | B2* | 11/2020 | Shi | G01R 33/3852 |
| 10,905,353 | B2* | 2/2021 | Chen | G01R 33/5608 |
| 10,916,337 | B2* | 2/2021 | Poblenz | G06F 9/542 |
| 10,977,390 | B2* | 4/2021 | Blumhofer | G06F 21/6254 |
| 10,979,461 | B1* | 4/2021 | Cervantez | H04L 63/105 |
| 11,062,449 | B2* | 7/2021 | Mao | G06T 7/11 |
| 11,089,970 | B2* | 8/2021 | Lindner | A61B 5/0042 |
| 11,355,224 | B2* | 6/2022 | Dror | G06F 16/2462 |
| 11,399,780 | B2* | 8/2022 | Wang | A61B 6/032 |
| 11,501,460 | B2* | 11/2022 | Rinck | G06T 7/70 |
| 11,509,628 | B2* | 11/2022 | Dror | H04L 63/0421 |
| 11,544,407 | B1* | 1/2023 | Sjöstrand | G06F 3/0486 |
| 11,593,519 | B2* | 2/2023 | Blumhofer | G06T 5/70 |
| 11,606,336 | B2* | 3/2023 | Farchy | G06F 21/6245 |
| 11,682,115 | B2* | 6/2023 | Vilsmeier | G06V 10/764 |
| | | | | 382/131 |
| 11,769,249 | B2* | 9/2023 | Meng | G06T 7/187 |
| | | | | 382/128 |
| 11,803,556 | B1* | 10/2023 | Samdani | G06F 16/24578 |
| 11,853,455 | B2* | 12/2023 | Dror | G06N 20/00 |
| 11,854,189 | B2* | 12/2023 | Greiser | A61B 5/4547 |
| 11,868,504 | B2* | 1/2024 | Farchy | G06F 16/24568 |
| 2002/0186818 | A1* | 12/2002 | Arnaud | G06Q 30/02 |
| | | | | 378/165 |
| 2004/0147840 | A1* | 7/2004 | Duggirala | G06T 7/0012 |
| | | | | 600/437 |
| 2004/0252870 | A1* | 12/2004 | Reeves | G06T 7/136 |
| | | | | 382/128 |
| 2005/0283450 | A1* | 12/2005 | Matsugu | G06N 3/049 |
| | | | | 706/20 |
| 2006/0149739 | A1* | 7/2006 | Myers | G06F 21/6227 |
| | | | | 707/999.009 |
| 2008/0015418 | A1* | 1/2008 | Jarrell | G16H 70/20 |
| | | | | 600/300 |
| 2008/0021834 | A1* | 1/2008 | Holla | G16H 80/00 |
| | | | | 705/51 |
| 2008/0205717 | A1* | 8/2008 | Reeves | G06T 11/008 |
| | | | | 382/128 |
| 2008/0267483 | A1* | 10/2008 | Zhan | G06V 10/24 |
| | | | | 382/131 |
| 2009/0177495 | A1* | 7/2009 | Abousy | G16H 40/67 |
| | | | | 705/3 |
| 2009/0222388 | A1* | 9/2009 | Hua | G06N 5/02 |
| | | | | 382/103 |
| 2014/0328452 | A1* | 11/2014 | Tsubota | G06T 11/005 |
| | | | | 378/7 |
| 2014/0341471 | A1* | 11/2014 | Ono | A61B 5/0042 |
| | | | | 382/173 |
| 2015/0031979 | A1* | 1/2015 | Rappaport | A61B 5/087 |
| | | | | 600/407 |
| 2015/0063667 | A1* | 3/2015 | Sprencz | A61B 6/5217 |
| | | | | 382/128 |
| 2015/0305706 | A1* | 10/2015 | Kanik | A61B 8/5223 |
| | | | | 600/443 |
| 2016/0000408 | A1* | 1/2016 | Matsunaga | A61B 8/463 |
| | | | | 600/443 |
| 2016/0019695 | A1* | 1/2016 | Chukka | G06T 7/0014 |
| | | | | 382/128 |
| 2016/0027175 | A1* | 1/2016 | Kim | G06T 7/0016 |
| | | | | 382/131 |
| 2016/0058400 | A1* | 3/2016 | Pang | A61B 6/032 |
| | | | | 378/156 |
| 2016/0104281 | A1* | 4/2016 | Grady | G06V 40/103 |
| | | | | 382/128 |
| 2016/0157815 | A1* | 6/2016 | Slak | A61B 8/5261 |
| | | | | 433/29 |
| 2016/0203281 | A1* | 7/2016 | Zalis | G16H 40/20 |
| | | | | 705/3 |
| 2016/0314588 | A1* | 10/2016 | Harper | G06F 16/447 |
| 2016/0343127 | A1* | 11/2016 | Miller | G06T 7/11 |
| 2017/0076043 | A1* | 3/2017 | Dormer | G16H 40/67 |
| 2017/0116497 | A1* | 4/2017 | Georgescu | G06N 3/006 |
| 2018/0025255 | A1* | 1/2018 | Poole | G06V 10/7788 |
| | | | | 382/131 |
| 2018/0033144 | A1* | 2/2018 | Risman | G06T 7/0014 |
| 2018/0046758 | A1 | 2/2018 | Gogin et al. | |
| 2018/0060535 | A1* | 3/2018 | Reicher | G16H 50/30 |
| 2018/0060691 | A1* | 3/2018 | Bernal | H04N 19/103 |
| 2018/0114595 | A1* | 4/2018 | Stern | G16H 80/00 |
| 2018/0204111 | A1* | 7/2018 | Zadeh | G06V 10/764 |
| 2019/0043611 | A1* | 2/2019 | Saalbach | G16H 30/20 |
| 2019/0087603 | A1* | 3/2019 | Dror | G06F 21/6245 |
| 2019/0287686 | A1* | 9/2019 | Takeda | G06F 21/6254 |
| 2020/0202989 | A1* | 6/2020 | Dror | G16H 30/20 |
| 2020/0226283 | A1* | 7/2020 | Dror | G16H 50/70 |
| 2021/0034783 | A1* | 2/2021 | Blumhofer | G16H 30/40 |
| 2021/0103678 | A1* | 4/2021 | Dror | G06F 21/606 |
| 2021/0133351 | A1* | 5/2021 | Farchy | G16H 10/60 |
| 2021/0158514 | A1* | 5/2021 | Greiser | A61B 5/055 |
| 2021/0158563 | A1* | 5/2021 | Rinck | G06T 7/70 |
| 2021/0224424 | A1* | 7/2021 | Blumhofer | G06F 21/6254 |
| 2021/0243162 | A1* | 8/2021 | Farchy | H04L 63/0421 |
| 2021/0266296 | A1* | 8/2021 | Dror | H04L 9/50 |
| 2022/0171878 | A1* | 6/2022 | Dror | G06F 21/6254 |
| 2022/0179994 | A1* | 6/2022 | Dror | G16H 40/67 |
| 2022/0179995 | A1* | 6/2022 | Dror | G06F 21/6209 |
| 2022/0215551 | A1* | 7/2022 | Vilsmeier | G06T 7/30 |
| 2022/0270730 | A1* | 8/2022 | Dror | G06F 16/2462 |
| 2023/0188501 | A1* | 6/2023 | Farchy | G06F 21/6245 |
| | | | | 726/1 |

FOREIGN PATENT DOCUMENTS

| | | |
|---|---|---|
| JP | 2017-224149 A | 12/2017 |
| JP | 2019-003413 A | 1/2019 |
| JP | 2019-3413 A | 1/2019 |

OTHER PUBLICATIONS

Office Action issued on Jun. 18, 2024 for the corresponding Japanese Patent Application No. 2021-035172 with an English translation, 8 pages.

Office Action, dated Sep. 10, 2024, issued for the corresponding Japanese Patent Application No. 2021-035172, with English Translation.

* cited by examiner

FIG. 3

| PATIENT ID | DATA ID |
|---|---|
| 202007120000 | 00000000 |
| 202007120001 | 00000001 |
| 202007120001 | 00000002 |
| 202008310000 | 00000003 |
| 202007120001 | 00000004 |

MEDICAL INFORMATION MANAGEMENT APPARATUS, MEDICAL INFORMATION MANAGEMENT METHOD, AND MEDICAL INFORMATION MANAGEMENT PROGRAM

The entire disclosure of Japanese patent Application No. 2021-035172, filed on Mar. 5, 2021, is incorporated herein by reference in its entirety.

BACKGROUND

Technological Field

The present invention relates to a medical information management apparatus, a medical information management method, and a medical information management program.

Description of the Related Art

In recent years, in the medical field, there is a trend to provide diagnostic support by machine learning such as AI for image diagnosis or the like performed by humans, or to replace the diagnostic action itself with one by machine learning. Machine learning is to use a large amount of data to make a machine learn patterns and correlations of data, so that various types of detection and the like can be performed.

In order to perform highly accurate detection by machine learning in the medical field, it is necessary to collect, as data used for learning, a lot of medical image data, information regarding patients who visited medical institutions (facilities such as hospitals) such as information regarding diagnosis, and the like (these are collectively called "medical information").

Information regarding patients (medical information) acquired at medical institutions contains a lot of highly personal information. Thus, from the viewpoint of personal information protection, in order to take out the medical information from a medical institution to the outside (for example, a development institution), it is necessary to perform anonymization processing in accordance with various laws and regulations so as not to include personal information.

JP 2012-217631 A and JP 2008-237426 A describe techniques for removing and storing personal information from diagnostic images (still images and/or dynamic images) included in examination data (medical information).

However, in the techniques described in JP 2012-217631 A and JP 2008-237426 A, when the user outputs medical information from an apparatus in order to provide the medical information to a third party, the user needs an operation for performing anonymization processing to remove the personal information from the medical image data stored for diagnosis. Thus, there has been a problem that the user mistakenly operates and outputs the medical information without removing the personal information, and moreover, the medical information may be taken to the outside in a state where the personal information included.

SUMMARY

An object of the present invention is to provide a medical information management apparatus, a medical information management method, and a medical information management program capable of preventing medical information from being taken to an outside in a state where personal information is included.

To achieve the abovementioned object, according to an aspect of the present invention, a medical information management apparatus reflecting one aspect of the present invention comprises a hardware processor that: generates first medical information that does not include subject identification information that uniquely identifies a subject on a basis of medical image information regarding the subject; generates second medical information that includes the subject identification information on a basis of the medical image information; and causes the first medical information that has been generated to be stored in a first medical information storage part.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 3 is a diagram illustrating an example of correspondence information; and

DETAILED DESCRIPTION OF EMBODIMENTS

Hereinafter, one or more embodiments of the present invention will be described with reference to the drawings. However, the scope of the invention is not limited to the disclosed embodiments.

Figure 1:
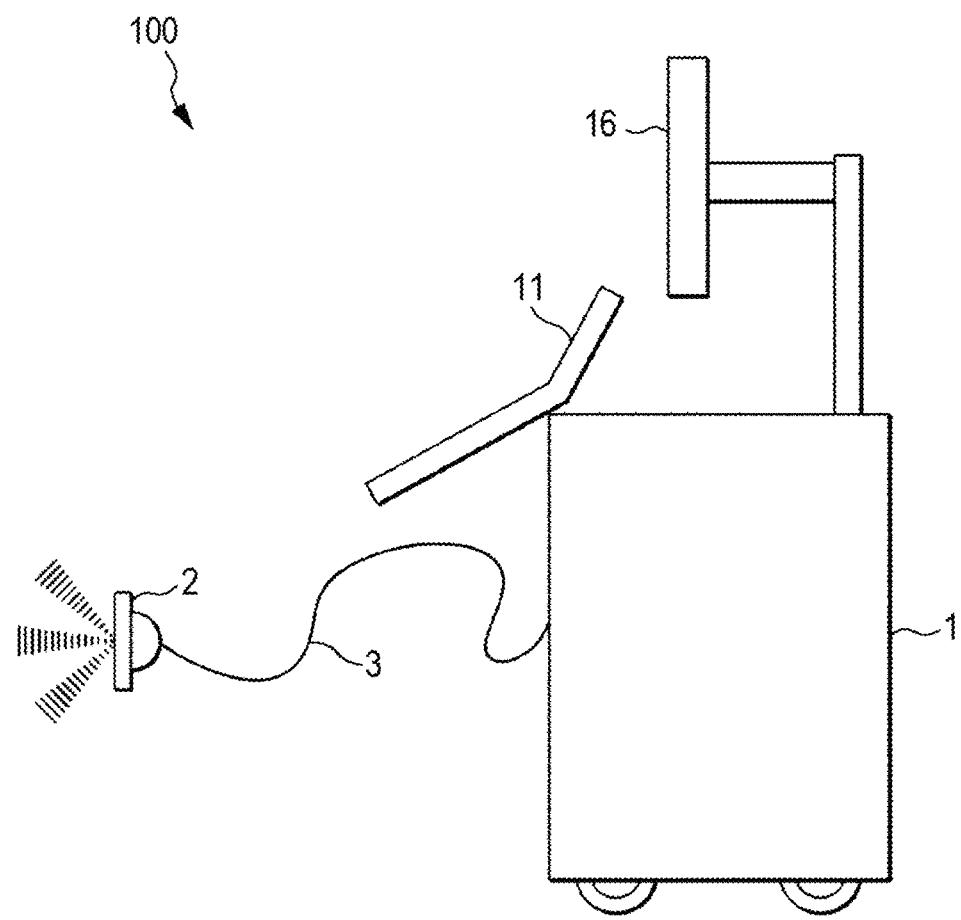
FIG. 1 is an external view of an ultrasonic image diagnostic apparatus.

Hereinafter, an ultrasonic image diagnostic apparatus 100 according to the present embodiment will be described in detail with reference to the drawings. FIG. 1 is an external view of the ultrasonic image diagnostic apparatus 100.

As illustrated in FIG. 1, the ultrasonic image diagnostic apparatus 100 includes an ultrasonic image diagnostic apparatus main body 1 and an ultrasonic probe 2. Note that the ultrasonic image diagnostic apparatus 100 functions as a "medical information management apparatus" according to the present invention.

The ultrasonic probe 2 transmits ultrasonic waves (transmission ultrasonic waves) to a subject such as a living body (for example, a patient) that is not illustrated, and receives reflected waves (reflected ultrasonic waves: echo) of the ultrasonic waves reflected in the subject.

The ultrasonic image diagnostic apparatus main body 1 is connected to the ultrasonic probe 2 via a cable 3, and causes the ultrasonic probe 2 to transmit transmission ultrasonic waves to the subject by transmitting a drive signal of an electric signal to the ultrasonic probe 2.

Further, the ultrasonic image diagnostic apparatus main body 1 images an internal state in the subject as an ultrasonic image on the basis of a reception signal that is an electric signal generated by the ultrasonic probe 2 in response to reflected ultrasonic waves from the inside of the subject received by the ultrasonic probe 2. Further, the ultrasonic image diagnostic apparatus main body 1 includes an operation input unit 11 and a display unit 16, which will be described later.

The ultrasonic probe 2 includes a transducer 2a (see FIG. 2) including a piezoelectric element. A plurality of transducers 2a is arranged in a one-dimensional array in an orientation direction (scanning direction), for example. In this embodiment, for example, an ultrasonic probe 2 having 192 transducers 2a is used.

Note that the transducers 2a may be arranged in a two-dimensional array. Further, the number of transducers 2a can be arbitrarily set. Further, in the present embodiment, a linear electron scan probe is used as the ultrasonic probe 2 to scan ultrasonic waves by a linear scanning method, but either a sector scanning method or a convex scanning method can also be employed. The communication between the ultrasonic image diagnostic apparatus main body 1 and the ultrasonic probe 2 may be performed by wireless communication using Ultra Wide Band (UWB) or the like instead of the wired communication via the cable 3.

Figure 2:
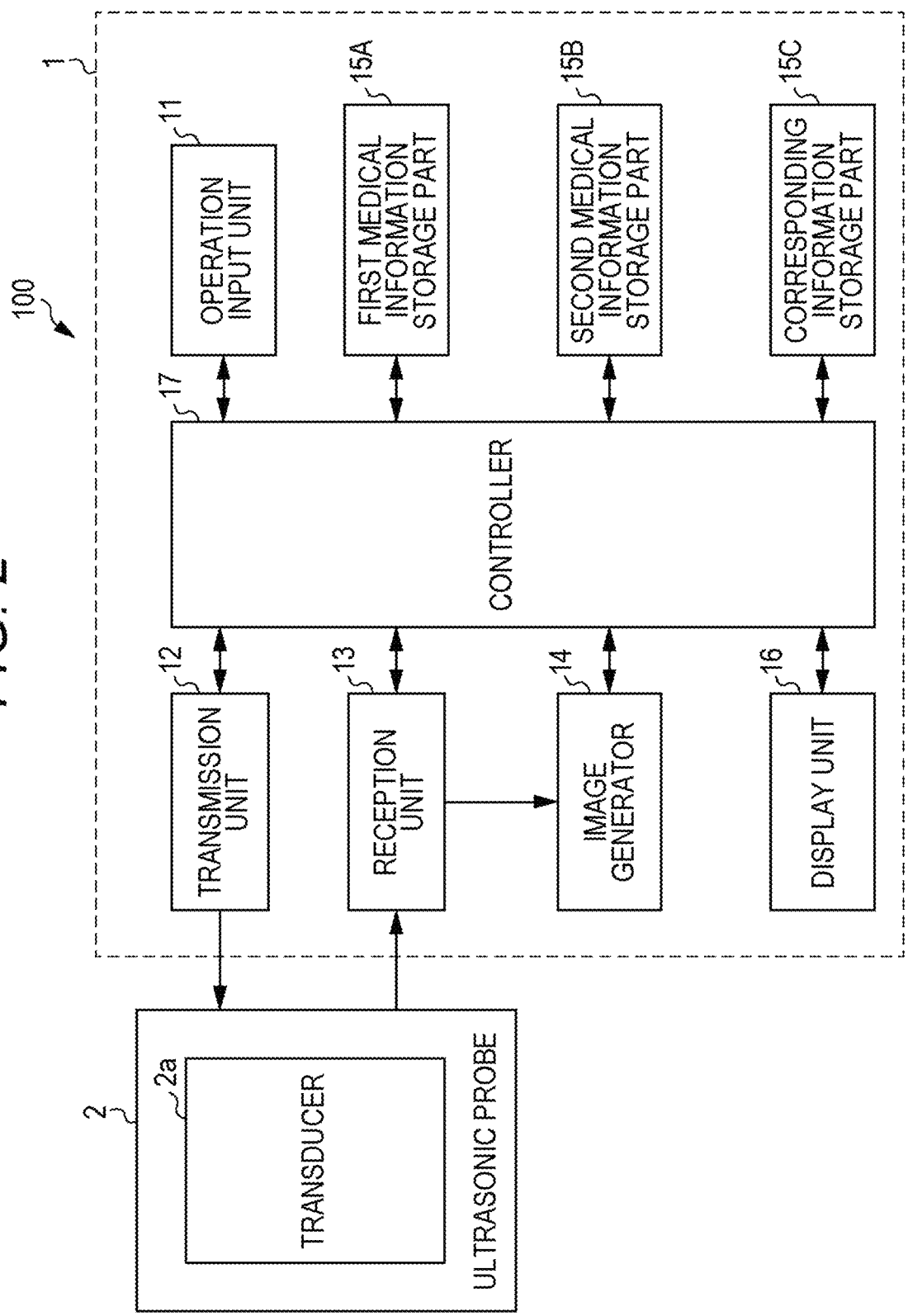
FIG. 2 is a block diagram illustrating a functional configuration of the ultrasonic image diagnostic apparatus.

Next, a functional configuration of the ultrasonic image diagnostic apparatus 100 will be described with reference to FIG. 2. FIG. 2 is a block diagram illustrating a functional configuration of the ultrasonic image diagnostic apparatus 100.

As illustrated in FIG. 2, the ultrasonic image diagnostic apparatus main body 1 includes, for example, an operation input unit 11, a transmission unit 12, a reception unit 13, an image generator 14, a first medical information storage part 15A, a second medical information storage part 15B, a correspondence information storage part 15C, a display unit 16, and a controller 17. Note that the controller 17 functions as a "first medical information generator", a "second medical information generator", a "storage controller", a "first storage area setter", a "storage setter", a "second storage area setter", a "generation setter", an "adder", and a "storage information setter" according to the present invention.

The operation input unit 11 includes various switches, buttons, a trackpad, a trackball, a mouse, a keyboard, and a touch panel or the like that is integrally provided on a display screen of the display unit 16 and detects a touch operation on the display screen. The operation input unit 11 inputs, for example, a command for instructing the start of diagnosis, data such as personal information of a subject, and various parameters for displaying an ultrasonic image on the display unit 16. Then, the operation input unit 11 outputs an operation signal corresponding to an input operation to the controller 17.

The transmission unit 12 is a circuit that supplies a drive signal, which is an electric signal, to the ultrasonic probe 2 via the cable 3 and causes the ultrasonic probe 2 to generate the transmission ultrasonic waves under control of the controller 17.

Further, the transmission unit 12 includes, for example, a clock generation circuit, a delay circuit, and a pulse generation circuit. The clock generation circuit is a circuit that generates a clock signal that determines a transmission timing and a transmission frequency of the drive signal. The delay circuit is a circuit for setting a delay time for each individual path corresponding to each transducer 2a, and delaying transmission of the drive signal by the set delay time for focusing a transmission beam including the transmission ultrasonic waves (transmission beam forming), and the like. The pulse generation circuit is a circuit for generating a pulse signal as the drive signal at a set voltage and a time interval.

The transmission unit 12 configured as described above sequentially switches the plurality of transducers 2a that supplies the drive signal while shifting a predetermined number for each transmission and reception of ultrasonic waves under control of the controller 17, and supplies a drive signal to the plurality of transducers 2a to which output is selected, thereby performing scanning.

The reception unit 13 is a circuit that receives a reception signal, which is an electric signal, from the ultrasonic probe 2 via the cable 3 under control of the controller 17. The reception unit 13 includes, for example, an amplifier, an A/D conversion circuit, and a phasing addition circuit.

The amplifier is a circuit for amplifying a reception signal at a preset amplification factor for each individual path corresponding to each transducer 2a. The A/D conversion circuit is a circuit for analog-to-digital conversion (A/D conversion) of the amplified reception signal. The phasing addition circuit adjusts a time phase by giving a delay time for each individual path corresponding to each transducer 2a to the A/D-converted reception signal, and adds (phasing addition) these reception signals to generate sound line data. That is, the phasing addition circuit performs reception beam forming on the reception signal for each transducer 2a to generate sound line data.

The image generator 14 performs envelope detection processing, logarithmic compression, and the like on the sound line data from the reception unit 13 under control of the controller 17, adjusts the dynamic range and gain, and performs brightness conversion, thereby generating brightness (B) mode image data (hereinafter, ultrasonic image data) as tomographic image data. That is, the ultrasonic image data (corresponding to the "medical image information regarding the subject" according to the present invention) represents intensity of the reception signal by brightness.

Further, the image generator 14 includes an image memory unit (not illustrated) including a semiconductor memory such as a dynamic random access memory (DRAM). The image generator 14 causes the generated ultrasonic image data to be stored in the image memory unit in frame units.

Further, the image generator 14 performs image processing such as image filtering processing and time smoothing processing on the ultrasonic image data read from the image memory unit, and scan-converts the ultrasonic image data into a display image pattern for display on the display unit 16.

The first medical information storage part 15A, the second medical information storage part 15B, and the correspondence information storage part 15C are internal storage parts internally capable of writing and reading information, such as a flash memory, a hard disk drive (HDD), or a solid state drive (SSD). The first medical information storage part 15A, the second medical information storage part 15B, and the correspondence information storage part 15C have, for example, different storage areas (storage destinations) such as a storage folder, a storage drive, and a memory storage.

The display unit 16 is a display device such as a liquid crystal display (LCD), a cathode-ray tube (CRT) display, an organic electronic luminescence (EL) display, an inorganic EL display, and a plasma display. The display unit 16 displays an ultrasonic image corresponding to the ultrasonic image data generated by the image generator 14 on the display screen under control of the controller 17.

The controller 17 includes, for example, a central processing unit (CPU), a read only memory (ROM), and a random access memory (RAM), and reads various processing programs such as a system program stored in the ROM and expands them in the RAM, and centrally controls operation of each part of the ultrasonic image diagnostic apparatus main body 1 according to the expanded program.

The ROM includes a non-volatile memory or the like of a semiconductor or the like, and stores a system program corresponding to the ultrasonic image diagnostic apparatus 100, various processing programs that can be executed on the system program, various data such as a gamma table, and the like. These programs are stored in the form of a computer-readable program code, and the CPU sequentially executes operations according to the program code. The RAM forms a work area that temporarily stores various programs executed by the CPU and data related to these programs. In the present embodiment, the "medical information management program" is stored in the ROM of the controller 17.

The controller 17 generates first medical information that does not include subject identification information (for example, patient ID, patient name, and the like) that uniquely identifies a subject corresponding to the ultrasonic image data on the basis of the ultrasonic image data generated by the image generator 14. Then, the controller 17 causes the generated first medical information to be stored in the first medical information storage part 15A. Note that the ultrasonic image data may be data in middle of being generated by the image generator 14, that is, before being imaged (for example, RAW data).

The first medical information stored in the first medical information storage part 15A is taken out as data used for the machine learning from the medical institution to the outside (for example, a development institution), in order to provide diagnostic support by machine learning such as AI for image diagnosis or the like performed by humans, and replace the diagnostic action itself with machine learning. Since the first medical information is stored in the first medical information storage part 15A in a form that does not include the subject identification information, it is not necessary to perform anonymization processing when the first medical information is taken to the outside.

Since the first medical information storage part 15A and the second medical information storage part 15B have different storage areas (storage destinations), when the first medical information is taken to the outside, the first medical information storage part 15A can be copied and taken out in its entirety. Note that the first medical information storage part 15A may be an external storage part (for example, a USB memory, a USB-connected SSD drive, or an SD card) of the ultrasonic image diagnostic apparatus 100. In this case, when the first medical information is taken out, the first medical information storage part 15A itself can be taken to the outside.

The first medical information includes ultrasonic image data (including RAW data before imaging), still images and dynamic images generated on the basis of the ultrasonic image data, information regarding a device used to generate the first medical information (in the present embodiment, the ultrasonic image diagnostic apparatus main body 1 and the ultrasonic probe 2), parameters related to generation of the first medical information, age information obtained by rounding the age of a living body (for example, a patient), gender information of the living body, and the like. Here, rounding the age of the living body means, for example, rounding in a predetermined unit such as twenties or thirties, or setting all ages equal to or more than a predetermined age (for example, 90 years old) or older to be this age or older. The reason for rounding the age of the living body is to eliminate the possibility that the living body is uniquely identified. Especially in a case of an extremely old living body, there is a possibility that the living body can be uniquely identified by only the age.

Note that the controller 17 may acquire the subject identification information from an electronic medical record device (not illustrated), or may generate the subject identification information on the basis of the operation signal output from the operation input unit 11.

Further, the controller 17 generates second medical information including subject identification information that uniquely identifies the subject corresponding to the ultrasonic image data on the basis of the ultrasonic image data generated by the image generator 14. Then, the controller 17 causes the generated second medical information to be stored in the second medical information storage part 15B. The second medical information stored in the second medical information storage part 15B is examination data used for diagnosis of a normal ultrasonic image.

Further, the controller 17 sets the storage area of the first medical information storage part 15A on the basis of the operation signal output from the operation input unit 11. Thus, a flexible response can be performed depending on a management operation mode of the first medical information, such as whether to store the first medical information in the internal storage part of the ultrasonic image diagnostic apparatus 100 or the external storage part of the ultrasonic image diagnostic apparatus 100. Note that if the set storage area of the first medical information storage part 15A is the same as that of the second medical information storage part 15B, the controller 17 may prohibit storage of the first medical information in the first medical information storage part 15A, may not accept this setting, or may output a warning. Thus, it is possible to securely prevent mixing of the first and second medical information in the same storage area.

Further, the controller 17 sets to enable or disable storage of the first medical information in the first medical information storage part 15A on the basis of the operation signal output from the operation input unit 11. It is not necessary to store (save) the first medical information in normal diagnosis of an ultrasonic image. Therefore, the controller 17 sets to enable storage of the first medical information in the first medical information storage part 15A only when the first medical information is taken to the outside for machine learning.

Further, the controller 17 sets information to be included in the first medical information to be stored in the first medical information storage part 15A. Thus, it is possible to set for each information which information is included in the first medical information. This is because when taking the first medical information to the outside, it is desirable not to include information unnecessary for machine learning as much as possible in relation to management of the first medical information.

Further, the controller 17 associates the subject identification information that uniquely identifies the subject corresponding to the ultrasonic image data with medical information identification information (for example, data ID) that uniquely identifies the first medical information, to thereby generate correspondence information. Then, the controller 17 causes the generated correspondence information to be stored in the correspondence information storage part 15C.

FIG. 3 is a diagram illustrating an example of correspondence information. As illustrated in FIG. 3, the correspondence information is a table associating the subject identification information (patient ID) that uniquely identifies the subject with the medical information identification information (data ID) that uniquely identifies the first medical information. Every time the diagnosis of an ultrasonic image is performed for the subject and the first medical information generated on the basis of the ultrasonic image data obtained as a result of the diagnosis is stored in the first medical information storage part 15A, the controller 17 adds a line associating the subject identification information (patient ID) with the medical information identification information (data ID) to the correspondence information. Note that the correspondence information does not have to associate the subject identification information with the medical information identification information in a tabular format.

As first information included in the correspondence information, the subject uniquely identified by a patient ID: 202007120000 and the first medical information uniquely identified by a data ID: 00000000 are associated with each other. This indicates that the diagnosis of an ultrasonic image is performed for the subject uniquely identified by the patient ID: 202007120000, and the first medical information uniquely identified by the data ID: 00000000 is generated on the basis of the ultrasonic image data obtained as a result of the diagnosis, and stored in the first medical information storage part 15A.

As second information included in the correspondence information, the subject uniquely identified by a patient ID: 202007120001 and the first medical information uniquely identified by a data ID: 00000001 are associated with each other. This indicates that the diagnosis of an ultrasonic image is performed for the subject uniquely identified by the patient ID: 202007120001, and the first medical information uniquely identified by the data ID: 00000001 is generated on the basis of the ultrasonic image data obtained as a result of the diagnosis, and stored in the first medical information storage part 15A.

As third information included in the correspondence information, the subject uniquely identified by a patient ID: 202007120001 and the first medical information uniquely identified by a data ID: 00000002 are associated with each other. This indicates that the diagnosis of an ultrasonic image is performed for the subject uniquely identified by the patient ID: 202007120001 (same as the second information), and the first medical information uniquely identified by the data ID: 00000002 is generated on the basis of the ultrasonic image data obtained as a result of the diagnosis, and stored in the first medical information storage part 15A.

As fourth information included in the correspondence information, the subject uniquely identified by a patient ID: 202008310000 and the first medical information uniquely identified by a data ID: 00000003 are associated with each other. This indicates that the diagnosis of an ultrasonic image is performed for the subject uniquely identified by the patient ID: 202008310000, and the first medical information uniquely identified by the data ID: 00000003 is generated on the basis of the ultrasonic image data obtained as a result of the diagnosis, and stored in the first medical information storage part 15A.

As fifth information included in the correspondence information, the subject uniquely identified by a patient ID: 202007120001 and the first medical information uniquely identified by a data ID: 00000004 are associated with each other. This indicates that the diagnosis of an ultrasonic image is performed for the subject uniquely identified by the patient ID: 202007120001 (same as the second and third information), and the first medical information uniquely identified by the data ID: 00000004 is generated on the basis of the ultrasonic image data obtained as a result of the diagnosis, and stored in the first medical information storage part 15A.

Note that the correspondence information may be a table associating a plurality of pieces of subject identification information (patient ID) with a plurality of pieces of medical information identification information (data ID), or may be a table associating a piece of subject identification information (patient ID) with a plurality of pieces of medical information identification information (data ID).

Generating and storing the above correspondence information enables that, when the patient (subject) later requests not to use his or her own ultrasonic image data for machine learning (development), the medical institution side can refer to the correspondence information, and identify the data ID corresponding to the patient ID of the patient. Then, the external development institution to which the first medical information with the personal information (subject identification information) removed is taken out can be told not to use the first medical information uniquely identified by this data ID for machine learning (development).

Further, the storage area (storage destination) is different between the first medical information storage part 15A and the correspondence information storage part 15C. Thus, in the same storage area, it is possible to securely prevent mixing of the correspondence information including the personal information (patient ID) and the first medical information not including the personal information (subject identification information).

Further, the controller 17 sets the storage area of the correspondence information storage part 15C on the basis of the operation signal output from the operation input unit 11. Thus, the storage area of the correspondence information storage part 15C can be flexibly changed according to the management operation mode of the correspondence information. Note that if the set storage area of the correspondence information storage part 15C is the same as that of the first medical information storage part 15A, the controller 17 may prohibit storage of the correspondence information in the correspondence information storage part 15C, may not accept the setting, or may output a warning. Thus, it is possible to securely prevent mixing of the correspondence information and the first medical information in the same storage area.

Further, the controller 17 sets to enable or disable generation of the correspondence information on the basis of the operation signal output from the operation input unit 11. The correspondence information includes personal information (patient ID) of the living body. Therefore, the controller 17 sets to enable generation of the correspondence information only when it is necessary to generate the correspondence information.

Further, the controller 17 generates the first medical information by removing the subject identification information from the display screen including the ultrasonic image corresponding to the ultrasonic image data.

Further, the controller 17 adds annotation information (for example, information regarding the target area of machine learning) to the ultrasonic image on the basis of the operation signal output from the operation input unit 11, and causes the first medical information including the annotation information to be stored in the first medical information storage part 15A. Thus, when the first medical information is taken out from the medical institution to the outside (for example, a development institution), the machine learning developer can perform appropriate machine learning by referring to the annotation information included in the first medical information.

Note that the controller 17 may cause the first medical information including the annotation information and the first medical information not including the annotation information to be stored in the first medical information storage part 15A, or may cause the annotation information and the first medical information to be separately stored in the first medical information storage part 15A.

Figure 4:
FIG. 4 is a diagram illustrating a display example based on first medical information.

FIG. 4 is a diagram illustrating a display example of the display screen 20 including the ultrasonic image corresponding to the ultrasonic image data.

In the display screen 20 illustrated in FIG. 4, the display area 21 is an area in which subject identification information (personal information such as patient ID and patient name) is displayed. In the display screen 20 illustrated in FIG. 4, in an area indicated by a round dotted line, for example, information as a hint to the developer side, such as information regarding the target area of machine learning, is displayed as the annotation information given to the ultrasonic image. The controller 17 generates the first medical information by removing the subject identification information from the display screen 20 including the ultrasonic image corresponding to the ultrasonic image data. For example, the controller 17 generates the first medical information by removing the subject identification information by masking (painting in black, and the like) an area where the subject identification information (personal information such as a patient ID and a patient name) is displayed on the display screen 20. Alternatively, the controller 17 generates the first medical information excluding the subject identification information by cutting the area including the display area 21 from the display screen 20 and including only the display area 22 in the first medical information.

As described in detail above, in the present embodiment, an ultrasonic image diagnostic apparatus 100 (medical information management apparatus) includes a first medical information generator (controller 17) that generates first medical information that does not include subject identification information that uniquely identifies a subject on a basis of medical image information regarding the subject, a second medical information generator (controller 17) that generates second medical information that includes the subject identification information on a basis of the medical image information, and a storage controller (controller 17) that causes the first medical information that has been generated to be stored in a first medical information storage part 15A.

According to the present embodiment configured in this manner, the first medical information that does not include subject identification information and the second medical information that includes the subject identification information are separately generated and the first medical information is stored in the first medical information storage part 15A in a form that does not include the subject identification information. Thus, when the ultrasonic image diagnostic apparatus 100 outputs the medical information in order to provide the medical information (first medical information) to a third party, the user does not need an operation for performing anonymization processing to remove the personal information from the ultrasonic image data stored for diagnosis. Therefore, it is possible to prevent the user from mistakenly operating and outputting the medical information without removing the personal information (subject identification information), and moreover, the medical information from being taken to the outside in a state where the personal information included.

Further, in the present embodiment, the storage controller (controller 17) generates correspondence information by associating the subject identification information that uniquely identifies the subject with medical information identification information that uniquely identifies the first medical information, and causes the correspondence information to be stored in a correspondence information storage part 15C.

According to the present embodiment configured in this manner, when the patient (subject) later requests not to use his or her own ultrasonic image data for machine learning (development), the medical institution side can refer to the correspondence information, and identify the data ID (medical information identification information) corresponding to the patient ID (subject identification information) of the patient. Then, the external development institution to which the first medical information with the personal information (subject identification information) removed is taken out can be told not to use the first medical information uniquely identified by this data ID for machine learning (development).

Note that in the above embodiment, an example in which the first medical information storage part 15A and the second medical information storage part 15B have different storage areas (storage destinations) has been described, but the present invention is not limited to this. The first medical information storage part 15A and the second medical information storage part 15B may have the same storage area.

Further, in the above embodiment, with respect to the transmission unit 12, the reception unit 13, the image generator 14, and the controller 17 included in the ultrasonic image diagnostic apparatus 100, a part or all of the functions of respective functional blocks can be achieved as a hardware circuit such as an integrated circuit or the like. The integrated circuit is, for example, a large scale integrated circuit (LSI), and the LSI may also be called an IC, a system LSI, a super LSI, or an ultra LSI depending on the degree of integration. Further, the circuit integration method is not limited to LSI and may be achieved by a dedicated circuit or a general-purpose processor, and a field programmable gate array (FPGA) or a reconfigurable processor capable of reconfiguring connections and settings of circuit cells inside the LSI may be used. Further, a part or all of the functions of each functional block may be executed by software. In this case, this software is stored in one or more storage media such as ROM, an optical disk, a hard disk, or the like, and this software is executed by an arithmetic processor.

Further, in the above embodiment, an example in which the ultrasonic image diagnostic apparatus 100 functions as the "medical information management apparatus" of the present invention has been described, but the present invention is not limited to this. For example, a Computed Radiography (CR) apparatus that captures X-ray image data of a subject by X-ray as medical image information using Imaging Plate (IP), a CT apparatus that captures tomographic image data of a subject by X-ray as medical image information, and an MRI apparatus that captures sectional image data of a subject by magnetization as medical image information may function as the "medical information management apparatus" according to the present invention.

Note that each of the above-described embodiments is merely an example of embodiments in carrying out the present invention, and the technical scope of the present invention should not be limitedly interpreted by these. That is, the present invention can be implemented in various forms without departing from the gist or main features thereof.

Although embodiments of the present invention have been described and illustrated in detail, the disclosed embodiments are made for purposes of illustration and example only and not limitation. The scope of the present invention should be interpreted by terms of the appended claims

What is claimed is:

1. A medical information management apparatus comprising
a hardware processor;
a correspondence information storage part; and
an operation inputter configured to receive a user input,
wherein the hardware processor
generates first medical information that does not include subject identification information that uniquely identifies a subject on a basis of medical image information regarding the subject, the first medical information includes a plurality of first medical information that does not include the subject identification information on a basis of medical information regarding at least one subject;
generates second medical information that includes the subject identification information on a basis of the medical image information, the second medical information include a plurality of second medical information that includes the subject identification information on a basis of the medical information;
assigns each first medical information of the plurality of first medical information with a unique medical information identification information and assigns each subject of the at least one subject with a unique subject identification information,
generates correspondence information for each of the plurality of first medical information by associating unique medical information identification information with the unique subject identification information of a corresponding subject of the at least one subject,
causes the correspondence information to be stored in the correspondence information storage part,
sets a storage area of a first medical information storage part, in which the first medical information is to be stored, based on a user input on the operation inputter; and
in response to determining the set storage area is a same memory as a second medical information storage part in which the second medical information is to be saved, prohibits storage of the first medical information in the first medical information storage part, rejects the set storage area, or outputs a warning.

2. The medical information management apparatus according to claim 1, wherein
the hardware processor causes the generated second medical information to be stored in a second medical information storage part having a storage area different from a storage area of the first medical information storage part.

3. The medical information management apparatus according to claim 1, wherein
the correspondence information storage part has a storage area different from a storage area of the first medical information storage part.

4. The medical information management apparatus according to claim 1, wherein
the hardware processor sets a storage area of the correspondence information storage part.

5. The medical information management apparatus according to claim 1, wherein
the hardware processor sets to enable or disable generation of the correspondence information.

6. The medical information management apparatus according to claim 1, wherein
the hardware processor generates the first medical information by removing the subject identification information from a display screen including the medical image information.

7. The medical information management apparatus according to claim 1, wherein
the hardware processor adds annotation information to the medical image information, and
the hardware processor causes the first medical information including the annotation information to be stored in the first medical information storage part.

8. The medical information management apparatus according to claim 7, wherein
the hardware processor causes the first medical information including the annotation information and the first medical information not including the annotation information to be stored in the first medical information storage part.

9. The medical information management apparatus according to claim 7, wherein
the hardware processor causes the annotation information and the first medical information to be stored separately in the first medical information storage part.

10. The medical information management apparatus according to claim 1, wherein
the first medical information includes age information obtained by rounding the age of a living body corresponding to the subject.

11. A medical information management method comprising:
generating, by a hardware processor of a medical information management apparatus, first medical information that does not include subject identification information that uniquely identifies a subject on a basis of medical image information regarding the subject, the first medical information includes a plurality of first medical information that does not include the subject identification information on a basis of medical information regarding at least one subject;
generating, by the hardware processor, second medical information that includes the subject identification information on a basis of the medical image information, the second medical information include a plurality of second medical information that includes the subject identification information on a basis of the medical information; and
assigning each first medical information of the plurality of first medical information with a unique medical information identification information and assigning each subject of the at least one subject with a unique subject identification information,
generating correspondence information for each of the plurality of first medical information by associating unique medical information identification information with the unique subject identification information of a corresponding subject of the at least one subject,
causing the correspondence information to be stored in a correspondence information storage part,
setting a storage area of a first medical information storage part, in which the first medical information is to be stored, based on a user input on an operation inputter; and
in response to determining the set storage area is a same memory as a second medical information storage part in which the second medical information is to be saved, prohibiting storage of the first medical information in the first medical information storage part, rejecting the set storage area, or outputting a warning.

12. In a medical information management apparatus having a hardware processor, a correspondence information storage part, and an operation inputter configured to receive a user input, a non-transitory recording medium storing a computer readable medical information management program causing the hardware processor to perform:

generating first medical information that does not include subject identification information that uniquely identifies a subject on a basis of medical image information regarding the subject, the first medical information includes a plurality of first medical information that does not include the subject identification information on a basis of medical information regarding at least one subject;

generating second medical information that includes the subject identification information on a basis of the medical image information, the second medical information include a plurality of second medical information that includes the subject identification information on a basis of the medical information;

assigning each first medical information of the plurality of first medical information with a unique medical information identification information and assigning each subject of the at least one subject with a unique subject identification information, generating correspondence information for each of the plurality of first medical information by associating unique medical information identification information with the unique subject identification information of a corresponding subject of the at least one subject, causing the correspondence information to be stored in the correspondence information storage part, setting a storage area of a first medical information storage part, in which the first medical information is to be stored, based on a user input on the operation inputter; and in response to determining the set storage area is a same memory as a second medical information storage part in which the second medical information is to be saved, prohibiting storage of the first medical information in the first medical information storage part, rejecting the set storage area, or outputting a warning.

* * * * *